United States Patent
Yachi et al.

(10) Patent No.: US 9,533,924 B2
(45) Date of Patent: Jan. 3, 2017

(54) METHOD FOR PRODUCING HYDROCARBON MATERIAL

(75) Inventors: Yoshihide Yachi, Tokyo (JP); Hideaki Miki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 500 days.

(21) Appl. No.: 14/008,464

(22) PCT Filed: Mar. 30, 2012

(86) PCT No.: PCT/JP2012/058509
§ 371 (c)(1),
(2), (4) Date: Sep. 27, 2013

(87) PCT Pub. No.: WO2012/133732
PCT Pub. Date: Oct. 4, 2012

(65) Prior Publication Data
US 2014/0024867 A1    Jan. 23, 2014

(30) Foreign Application Priority Data
Mar. 31, 2011   (JP) ................................ 2011-079067

(51) Int. Cl.
| | | |
|---|---|---|
| *C07C 5/05* | (2006.01) | |
| *C10G 45/06* | (2006.01) | |
| *C10G 45/32* | (2006.01) | |
| *C10G 45/36* | (2006.01) | |
| *C10G 69/06* | (2006.01) | |
| *C10L 1/06* | (2006.01) | |
| *C10G 9/00* | (2006.01) | |
| *C07C 4/04* | (2006.01) | |

(52) U.S. Cl.
CPC . *C07C 5/05* (2013.01); *C07C 4/04* (2013.01); *C10G 9/00* (2013.01); *C10G 45/06* (2013.01); *C10G 45/32* (2013.01); *C10G 45/36* (2013.01); *C10G 69/06* (2013.01); *C10L 1/06* (2013.01); *C10G 2300/202* (2013.01); *C10G 2400/02* (2013.01); *C10G 2400/20* (2013.01)

(58) Field of Classification Search
CPC ............. C07C 5/05; C07C 5/07; C10G 45/02; C10G 45/32
USPC .......... 208/89, 142, 143, 144; 585/259, 260, 585/261, 262
See application file for complete search history.

(56) References Cited

U.S. PATENT DOCUMENTS

| | | | | |
|---|---|---|---|---|
| 4,113,603 A | * | 9/1978 | Bauer ................... | C10G 45/08 208/212 |
| 9,260,670 B2 | * | 2/2016 | Grenoble ............... | C10G 45/02 585/259 |
| 2008/0020926 A1 | | 1/2008 | Guillaume et al. | |
| 2010/0087692 A1 | | 4/2010 | Yoshimura et al. | |
| 2010/0300932 A1 | | 12/2010 | Debuisschert et al. | |

FOREIGN PATENT DOCUMENTS

| | | |
|---|---|---|
| JP | 6-104628 A | 4/1994 |
| JP | 2004-323485 A | 11/2004 |
| JP | 2005-213419 A | 8/2005 |
| JP | 2007-326955 A | 12/2007 |
| JP | 2008-23524 A | 2/2008 |
| JP | 2008-266438 A | 11/2008 |
| JP | 2010-202696 A | 9/2010 |
| JP | 2010-275550 A | 12/2010 |

OTHER PUBLICATIONS

Singaporean Examination Report, dated May 22, 2015, for Singaporean Application No. 2013070693.
International Search Report issued in PCT/JP2012/058509 mailed Jun. 19, 2012.

* cited by examiner

*Primary Examiner* — Sharon Pregler
(74) *Attorney, Agent, or Firm* — Birch, Stewart, Kolasch & Birch, LLP

(57) ABSTRACT

A method for producing a hydrocarbon material from a $C_5$ raffinate which is obtained as an extracted residual oil after separating at least part of the isoprene by extraction distillation from a $C_5$ fraction which is produced as a byproduct when thermally cracking naphtha to produce ethylene and has $C_5$ organic compounds as main ingredients comprising, a gas-phase thermal cracking step of gasifying the $C_5$ raffinate to thermally crack at least part of the $C_{10}$ diolefins which are contained in the gasified $C_5$ raffinate, a desulfurization step, after the gas-phase thermal cracking step, of removing at least part of the sulfur-containing ingredients which are contained in the gasified $C_5$ raffinate after the gas-phase thermal cracking step in the gas-phase state, and a hydrogen addition step, after the desulfurization step, of hydrogenating at least part of the carbon-carbon double bonds of at least one selected from diolefins and olefins which are contained in the gasified $C_5$ raffinate after the desulfurization step in the gas-phase state, so as to obtain a hydrocarbon material with a total concentration of diolefins and olefins of 0.5 wt % or less is provided.

7 Claims, No Drawings

METHOD FOR PRODUCING HYDROCARBON MATERIAL

TECHNICAL FIELD

The invention relates to a method for producing a hydrocarbon material from a $C_5$ raffinate which is obtained as an extracted residual oil after separating at least part of the isoprene by extraction distillation from a $C_5$ fraction which is produced as a byproduct when thermally cracking naphtha to produce ethylene and has $C_5$ organic compounds as main ingredients.

BACKGROUND ART

An isoprene which is a main material of a synthetic rubber etc. is usually obtained by extraction distillation of isoprene contained in a $C_5$ fraction which is extracted by an ethylene cracker of an ethylene center.

In the process of extraction distillation of the isoprene contained in a $C_5$ fraction, by removing the cyclopentadiene from the $C_5$ fraction by dimerization (forming dicyclopentadiene), then each removing light fractions such as pentanes and pentenes and heavy fractions such as pentadienes (including dicyclopentadiene and 1,3-pentadiene) and acetylenes by two distillation towers, and further removing diolefins (including 1,3-pentadiene) and remaining acetylenes by a next extraction distillation tower, then distilling the residue, it is possible to efficiently obtain isoprene from the tower bottom.

At this time, $C_5$ raffinate which is the extracted residual oil is obtained, but it is possible to return the $C_5$ raffinate to the ethylene center and mainly utilize it as a gasoline base material or raw material of the ethylene cracker. Further, the removed dicyclopentadiene, 1,3-pentadiene, etc. may be utilized as a raw material of a resin etc.

In this regard, each a concentration of the isoprene, dicyclopentadiene, 1,3-pentadiene, etc. in the $C_5$ fraction is generally constant, so demand for products using each as a raw material does not necessarily match each a ratio of concentration. Accordingly, sometimes the remainder is returned to the $C_5$ raffinate. Therefore, the concentration of diolefins in the $C_5$ raffinate which is returned to the ethylene center sometimes fluctuates at the level of several tens of percent.

Further, the $C_5$ fraction contains sulfur-containing ingredients in a concentration of several weight ppm to several hundred weight ppm. Therefore, the $C_5$ raffinate which is the extracted residual oil also contains sulfur-containing ingredients in several weight ppm to several hundred weight ppm.

Therefore, when using a $C_5$ raffinate as the raw material of an ethylene cracker, there are the problems that if the $C_5$ raffinate contains large amounts of sulfur-containing ingredients and diolefins as explained above, the catalyst in the diene removing tower which is installed at the refining section of the ethylene plant at the ethylene center remarkably deteriorates, the amount of consumption of hydrogen at the refining section greatly increases, and the profitability of the ethylene plant ends up deteriorating. Further, most of diolefins are high in polymerizability and their polymers easily form initiating substances causing fouling in the cooling pipes, so if diolefins are included in large amounts, there is also the problem that an increase in the frequency of cleaning of the cooling pipes is invited. Further, the catalyst in the diene removing tower end up being poisoned by the sulfur-containing ingredients, so if the sulfur-containing ingredients are included in large amounts, there is also the problem that a need arises for regenerating or replacing the poisoned catalyst and the running costs of the catalyst deteriorates.

For this reason, a $C_5$ raffinate which contains diolefins and sulfur-containing ingredients in large amounts has problems in terms of both quality and cost, so at the present time cannot be utilized as a hydrocarbon material, in particular a hydrocarbon material of an ethylene cracker, and is being burned as fuel.

On the other hand, due to the recent rising interest in environmental issues, the increase in carbon dioxide has become a concern. The need for effective utilization of crude oil has been rising. Therefore, it is desirable to utilize the $C_5$ raffinate as a hydrocarbon material rather than burning it.

For this reason, to use a $C_5$ raffinate which contains diolefins at a concentration of several tens of percent and contains sulfur-containing ingredients in an amount of several weight ppm to several hundred weight ppm as a hydrocarbon material for, in particular, an ethylene cracker, it is necessary to remove the sulfur-containing ingredients as much as possible and hydrogenate double bonds of the diolefins and olefins etc. as much as possible.

As opposed to this, for example, Patent Document 1 and Patent Document 2 disclose a method of selective hydrogenation of thermally cracked gasoline which uses a reaction tube packed with solid metal catalysts for selective hydrogenation by a first stage catalyst comprised of a palladium-based catalyst and a second stage catalyst comprised of a cobalt-molybdenum-based catalyst.

However, with the method described in Patent Document 1 and Patent Document 2, there are the problems that the hydrogenation is performed under a high pressure and the productivity is inferior. Further, the Patent Document 1 and Patent Document 2 do not describe anything about the effect of desulfurization. Further, they do not describe anything regarding the lifetimes of the catalysts which are used at the time of selective hydrogenation.

PRIOR ART DOCUMENTS

Patent Documents

Patent Document 1: Japanese Patent Publication No. 6-104628B

Patent Document 2: Japanese Patent Publication No. 2004-323485A

SUMMARY OF THE INVENTION

Problem to be Solved by the Invention

The present invention was made in consideration of such an actual situation and has as its object the provision of a method for producing a hydrocarbon material which obtains a hydrocarbon material from a $C_5$ raffinate during which it efficiently removes diolefins and olefins and sulfur-containing ingredients in the $C_5$ raffinate and extends the lifetimes of the catalysts to improve the productivity. Further, the present invention has as its object the provision of a high quality hydrocarbon material which is obtained by such a producing method.

Means for Solving the Problems

The inventors engaged in intensive research for achieving the above-mentioned objects and as a result discovered that by thermally cracking a $C_5$ raffinate in a gaseous state, then desulfurizing and hydrogenating it in a gaseous state, it is possible to efficiently remove the diolefins and olefins and sulfur-containing ingredients in the $C_5$ raffinate and extend the lifetimes of the catalysts, due to this, it is possible to improve the productivity and thereby completed the present invention.

That is, according to the present invention, there is provided a method for producing a hydrocarbon material from a $C_5$ raffinate which is obtained as an extracted residual oil after separating at least part of the isoprene by extraction distillation from a $C_5$ fraction which is produced as a byproduct when thermally cracking naphtha to produce ethylene and has $C_5$ organic compounds as main ingredients comprising a gas-phase thermal cracking step of gasifying the $C_5$ raffinate to thermally crack at least part of the $C_{10}$ diolefins which are contained in the gasified $C_5$ raffinate, a desulfurization step, after the gas-phase thermal cracking step, of removing at least part of the sulfur-containing ingredients which are contained in the gasified $C_5$ raffinate after the gas-phase thermal cracking step in the gas-phase state, and a hydrogen addition step, after the desulfurization step, of hydrogenating at least part of the carbon-carbon double bonds of at least one selected from diolefins and olefins which are contained in the gasified $C_5$ raffinate after the desulfurization step in the gas-phase state, so as to obtain a hydrocarbon material with a total concentration of diolefins and olefins of 0.5 wt % or less.

In the present invention, preferably the desulfurization step is performed in a reducing atmosphere under conditions of a pressure of 0.3 MPa or less and a temperature of 180 to 400° C.

In the present invention, preferably the desulfurization step is performed using a catalyst having a supported nickel as a main ingredient.

In the present invention, preferably the hydrogen addition step is performed in a reducing atmosphere under conditions of a pressure of 0.3 MPa or less and a temperature of 140 to 400° C.

In the present invention, preferably the hydrogen addition step is performed using a catalyst having a supported nickel as a main ingredient.

In the present invention, preferably the $C_5$ raffinate contains dicyclopentadiene in 10 wt % or more.

Further, according to the present invention, there is provided a hydrocarbon material which is obtained by any of the above methods. The hydrocarbon material of the present invention is preferably used as a raw material for an ethylene cracker or gasoline base material.

Effects of the Invention

According to the present invention, it is possible to obtain a hydrocarbon material from a $C_5$ raffinate during which it is possible to efficiently remove the diolefins and olefins and sulfur-containing ingredients in the $C_5$ raffinate and extend the lifetimes of the catalysts so as to improve the productivity.

DESCRIPTION OF EMBODIMENTS

Below, the present invention will be explained in detail.
The method for producing a hydrocarbon material of the present invention is a method for producing a hydrocarbon material from a $C_5$ raffinate which includes a later explained gas-phase thermal cracking step, desulfurization step, and hydrogen addition step.

The $C_5$ raffinate used in the present invention is a fraction which is obtained as an extracted residual oil after separating at least part of the isoprene by extraction distillation from a $C_5$ fraction which is produced as a byproduct when thermally cracking naphtha to produce ethylene and has $C_5$ organic compounds as main ingredients.

Here, since the $C_5$ raffinate used in the present invention is the fraction which is obtained as an extracted residual oil after separating at least part of the isoprene by extraction distillation from a $C_5$ fraction having $C_5$ organic compounds as main ingredients, at the time of extraction distillation of isoprene, sometimes part of the isoprene remains. For this reason, the $C_5$ raffinate used in the present invention may also contain isoprene.

Further, the $C_5$ raffinate used in the present invention need only be a fraction which is obtained as an extracted residual oil after separating at least part of the isoprene by extraction distillation, but it is preferably a fraction which is obtained as an extracted residual oil after each separating at least part of the three ingredients of isoprene plus dicyclopentadiene and 1,3-pentadiene by extraction distillation. In this case as well, at the time of extraction distillation of each ingredient, sometimes part of the three ingredients of the isoprene, dicyclopentadiene, and 1,3-pentadiene may each remain. For this reason, the $C_5$ raffinate used in the present invention may include isoprene, dicyclopentadiene, and 1,3-pentadiene. Note that, as the $C_5$ raffinate, one in which the portions of the separated isoprene, dicyclopentadiene, and 1,3-pentadiene for which there is no foreseeable use (surplus parts) are mixed in the extracted residual oil is also included.

Further, in the present invention, the method of extraction distillation of isoprene, dicyclopentadiene, and 1,3-pentadiene from the $C_5$ fraction having $C_5$ organic compounds as main ingredients is not particularly limited, but, for example, it is possible to employ the known method such as GPI process (Zeon Corporation).

As the $C_5$ raffinate used in the present invention, one which contains a $C_{10}$ diolefin comprised of dicyclopentadiene in 10 wt % or more is preferable and one which contains it in 30 wt % or more is more preferable, while one which contains 70 wt % or less is preferable and one which contains 60 wt % or less is more preferable. Further, as the $C_5$ raffinate used in the present invention, the content ratio of diolefins is preferably 10 wt % or more, more preferably 30 wt % or more, while it is preferably 70 wt % or less, more preferably 60 wt % or less. Further, in the $C_5$ raffinate used in the present invention, the content ratio of sulfur atoms (sulfur and sulfur atoms in sulfur-containing ingredients) is preferably 10 weight ppm or more with respect to the $C_5$ raffinate as a whole, more preferably 30 weight ppm or more, while is preferably 500 weight ppm or less, more preferably 300 weight ppm or less. By using a $C_5$ raffinate with content ratios of dicyclopentadiene, diolefins, and sulfur atoms in the above-mentioned ranges, the advantageous effects of the present invention can be made more remarkable.

<Gas-Phase Thermal Cracking Step>

Next, the gas-phase thermal cracking step will be explained. The gas-phase thermal cracking step is the step of gasifying the above-mentioned $C_5$ raffinate to thermally crack at least part of the $C_{10}$ diolefins contained in the gasified $C_5$ raffinate.

In the gas-phase thermal cracking step, first, the $C_5$ raffinate is heated to gasify it. For example, as the method of heating and gasifying the $C_5$ raffinate, the method of feeding the $C_5$ raffinate to a preheater which is provided in the reaction apparatus to preheat it, then feeding it to a gasifier joined with the preheater by piping to heat it may be mentioned. The heating temperature is usually 180 to 400° C.

Note that, when gasifying the $C_5$ raffinate, it is possible to add a diluent, entrainer (additive), etc.

Such a diluent and entrainer is not particularly limited so long as one which does not impair the thermal cracking reaction in the gas-phase thermal cracking step, the desulfurization reaction in the later explained desulfurization step, and the hydrogenation reaction in the later explained hydrogen addition step.

As specific examples of the diluents, inert gas such as nitrogen gas, helium gas, and argon gas; $C_5$ to $C_{10}$ alkanes such as n-pentane, n-hexane, and n-heptane; $C_5$ to $C_{10}$ cycloalkanes such as cyclopentane, cyclohexane, and cycloheptane; $C_5$ to $C_{10}$ alkenes such as 1-pentene, 2-pentene, 1-hexene, 2-hexene, and 1-heptene; $C_5$ to $C_{10}$ cycloalkenes such as cyclopentene, cyclohexene, and cycloheptene; etc. may be mentioned. Among these as well, ones with a boiling point of 40 to 300° C. in range is preferable.

As the entrainer, since it is necessary to dissolve high boiling point impurities, one with a boiling point of 150° C. or more is desirable. Specifically, a mineral oil-based and synthetic lubrication oil and thermal medium oil etc. may be mentioned.

The amounts of use of the diluent and entrainer are not particularly limited, but usually are 0 to 3000 part by weight with respect to 100 parts by weight of the $C_5$ raffinate, preferably 0 to 2000 part by weight, more preferably 0 to 1000 part by weight. If the amounts of use of the diluent and entrainer are too large, they sometimes become disadvantageous in terms of the process efficiency.

Next, the gasified $C_5$ raffinate is fed to the thermal cracker where treatment is performed to thermally crack at least part of the $C_{10}$ diolefins which are contained in the gasified $C_5$ raffinate. Note that, as the $C_{10}$ diolefins, for example, dicyclopentadiene may be mentioned. In this case, due to the thermal cracking reaction, the dicyclopentadiene which is contained in the gasified $C_5$ raffinate is cracked to cyclopentadiene. By thermally cracking the gasified $C_5$ raffinate in this way, even if the $C_5$ raffinate contains $C_{10}$ diolefins in a high concentration, the hydrogenation reaction in the later explained hydrogen addition step efficiently progresses and as a result it is possible to efficiently remove the diolefins and olefins in the obtained hydrocarbon material.

The temperature at the time of thermal cracking is usually 200 to 500° C., preferably 310 to 450° C. Further, the pressure at the time of thermal cracking is, in gauge pressure, preferably 0.5 MPa or less, more preferably 0.3 MPa or less, while is preferably 0 MPa or more.

Further, the time for thermal cracking is not particularly limited so long as, for example, the residence time (based on gas) inside the thermal cracker is made a range giving a predetermined cracking rate when performing thermal cracking in a thermal cracker, but is preferably 0.01 to 60 seconds, more preferably 0.05 to 40 seconds.

Further, by such a gas-phase thermal cracking step, it is possible to obtain gasified $C_5$ raffinate in which at least part of the $C_{10}$ diolefins contained in the $C_5$ raffinate is cracked (below, sometimes referred to as the "cracked gasified $C_5$ raffinate").

By such a gas-phase thermal cracking step, the content ratio of the $C_{10}$ diolefins in the cracked gasified $C_5$ raffinate can be reduced to preferably 1 wt % or less, more preferably 0.5 wt % or less, particularly preferably 0.1 wt % or less.

<Desulfurization Step>

Next, the desulfurization step will be explained. The desulfurization step is the step of removing at least part of the sulfur-containing ingredients which are contained in the gasified $C_5$ raffinate after the above-mentioned gas-phase thermal cracking step in the gas phase state.

In the desulfurization step, the desulfurization reaction is preferably performed in the presence of a catalyst. Usually, this is performed by feeding the cracked gasified $C_5$ raffinate obtained in the above-mentioned gas-phase thermal cracking step into the desulfurization reactor in which the catalyst is packed. The catalyst is not particularly limited, but in the present invention, use of a catalyst which has a supported nickel as its main ingredient is preferable.

The catalyst which has a supported nickel as its main ingredient is a catalyst which comprises compound having a support comprised of a supporting inorganic compound on which a metal comprised of nickel is supported as its main ingredient. As specific examples of the support comprised of a supporting inorganic compound, silica, alumina, boria, silica-alumina, diatomaceous earth, white clay, clay, magnesia, magnesia-silica, titania, zirconia, etc. may be mentioned. Among these as well, diatomaceous earth is preferable from the viewpoint of the higher desulfurization performance. That is, in the desulfurization step, a catalyst which comprises, as a main ingredient, a compound where nickel is supported on diatomaceous earth is preferable. By using such a catalyst, it is possible to efficiently remove the sulfur-containing ingredients which are contained in cracked gasified $C_5$ raffinate. Further, it is possible to maintain the desulfurization performance over a long time, so the productivity can be improved.

Further, as the metal which is supported on the support, nickel alone can realize a sufficient desulfurization performance, but from the viewpoint of being able to raise the desulfurization performance more, in addition to nickel, at least one type of metal which is selected from the group consisting of palladium, platinum, ruthenium, copper, chromium, molybdenum, zinc, and cobalt is preferably contained. From the viewpoint of being able to further raise the desulfurization performance, including copper and chromium in addition to nickel is particularly preferable. Note that, in this case, the content ratio of nickel is preferably 60 to 99.5 wt % with respect to the metal which is supported on the support as a whole, more preferably 80 to 99 wt %, furthermore preferably 90 to 95 wt %. On the other hand, the content ratio of the metals other than nickel is preferably 0.5 to 40 wt % with respect to the metal which is supported on the support as a whole, more preferably 1 to 20 wt %, furthermore preferably 5 to 10 wt %. If the content of the metals other than nickel is too small, sometimes the effect of improvement of the desulfurization performance becomes hard to obtain. On the other hand, if too large, sometimes the desulfurization performance ends up falling compared with the case when used as nickel alone. Note that, even when including two or more types of metal as the metals other than nickel, the total content ratio of the metals other than nickel may be made the above-mentioned range.

The content ratio of the metal which is supported on the support with respect to the catalyst as a whole is preferably 20 to 90 wt %, more preferably 40 to 70 wt %. On the other hand, the content ratio of the support comprised of the supporting inorganic compound with respect to the catalyst as a whole is preferably 80 to 10 wt %, more preferably 60 to 30 wt %. If the content of the metal which is supported on the support is too small, sometimes it becomes difficult for the desulfurization performance to be maintained for a long time. On the other hand, if too large, sometimes the mechanical strength of the catalyst itself falls and a sufficient desulfurization performance cannot be exhibited.

Further, the shape of the catalyst is not particularly limited and in general is a pellet shape, spherical shape, columnar shape, ring shape, etc. Further, the particle size of the catalyst is also not particularly limited. It is sufficient to select the optimum value according to the inside diameter of the desulfurization reactor etc., but the average particle size of the catalyst used in the present invention, from the viewpoint of efficient progress of the desulfurization reaction, is preferably 1 to 40 mm, more preferably 2 to 20 mm.

In the desulfurization step, the desulfurization reactor which is used is not particularly limited, but a multitube type fixed bed circulation reactor is preferable. Further, the inside diameter of the reaction tubes of the multitube type fixed bed circulation reactor is preferably 6 to 100 mm, more preferably 10 to 70 mm, while the length of the reaction tubes is preferably 0.1 to 10 m, more preferably 0.3 to 7 m.

In the desulfurization step, as pretreatment of the desulfurization reaction, it is preferable to reduce the catalyst which is packed in the desulfurization reactor in advance in the desulfurization reactor by a known method etc. By reducing the catalyst in advance, it is possible to raise the activity of the catalyst more. Further, due to this, it is possible to raise the efficiency of removal of the sulfur-containing ingredients in the desulfurization step more and further possible to extend the lifetime of the catalyst more.

The method of reducing the catalyst in advance is not particularly limited, but, for example, the method of inserting the catalyst in a desulfurization reactor and running reducing gas such as hydrogen to the desulfurization reactor in which the catalyst is inserted while heating the desulfurization reactor so as to heat and reduce the catalyst which is placed in the desulfurization reactor etc. may be mentioned.

The heating temperature of the catalyst in the reduction treatment is not particularly limited, but, for example, when using a catalyst which has a supported nickel as its main ingredient, it is usually 200 to 500° C. By making the heating temperature this range, it is possible to suitably improve the catalyst activity.

Further, the heating time of the catalyst at the time of reduction treatment is not particularly limited, but, for example, when using a catalyst which has a supported nickel as its main ingredient, it is preferably 1 hour or more, more preferably 3 hours or more. By making the heating time this range, it is possible to make the activation of the catalyst by reduction treatment sufficient.

Further, the gas hourly space velocity of hydrogen (value of total flow rate of hydrogen gas per hour divided by packed volume of catalyst (based on empty tube), below, referred to as "GHSV") at the time of reduction treatment is not particularly limited, but, for example, when using a catalyst which has a supported nickel as its main ingredient, 100 to 10000/hour is preferable, 200 to 5000/hour is more preferable.

In the desulfurization step, the desulfurization reaction is preferably performed in a reducing atmosphere, particularly preferably is performed in a hydrogen gas atmosphere. By performing the desulfurization reaction in a hydrogen gas atmosphere, it is possible to raise the efficiency of the desulfurization reaction more. The gas hourly space velocity (GHSV) of hydrogen in the case of performing the desulfurization reaction in a hydrogen gas atmosphere is not particularly limited, but 100 to 10000/hour is preferable, 200 to 5000/hour is more preferable.

In the present invention, by performing the desulfurization reaction using, as a catalyst, a catalyst which has a supported nickel as the main ingredient in a reducing atmosphere, it is possible to make not only the desulfurization reaction, but also the later explained hydrogenation reaction proceed. Further, in this case, in the desulfurization step, it is possible to make a hydrogenation reaction proceed to a certain extent at the same time as desulfurization and, in the next hydrogen addition step, make the hydrogenation reaction proceed substantially completely. Due to this, it becomes possible to more efficiently reduce the concentration of diolefins and olefins in the finally obtained hydrocarbon material. Further, for example, even when the reactivity of the hydrogenation reaction of the catalyst used in the desulfurization step deteriorates due to the effect of the sulfur-containing ingredients, it is possible to perform the hydrogenation reaction using a catalyst not poisoned by the sulfur-containing ingredients in the hydrogen addition step after the desulfurization step, so in such a case as well, it is possible to effectively reduce the concentration of diolefins and olefins in the finally obtained hydrocarbon material. Further, by providing the desulfurization step before the hydrogen addition step, it is possible to efficiently remove the sulfur-containing ingredients which are contained in the cracked gasified $C_5$ raffinate, so the hydrogenation catalyst becomes resistant to being poisoned by the sulfur-containing ingredients, the lifetimes of the catalysts can be remarkably increased, and the productivity can be improved.

The temperature of the desulfurization reaction is not particularly limited, but from the viewpoint of efficient progress in the desulfurization reaction, it is preferably 180 to 400° C., more preferably 190 to 350° C., furthermore preferably 200 to 320° C.

Further, the pressure of the desulfurization reaction is, by gauge pressure, preferably 0.3 MPa or less, more preferably 0.1 MPa or less, furthermore preferably 0.05 MPa or less, while is preferably 0 MPa or more. If the pressure of the desulfurization reaction is too high, there is the inconvenience that the ingredients which are contained in the cracked gasified $C_5$ raffinate and which are thermally cracked in the gas-phase thermal cracking step (for example, cyclopentadiene) end up undergoing a dimerization reaction and returning to $C_{10}$ diolefins (for example, dicyclopentadiene) before thermal cracking. Further, if ending up returning to $C_{10}$ diolefins before thermal cracking, hydrogenation at the later explained hydrogen addition step ends up becoming difficult. As a result, the content ratios of diolefins and olefins in the obtained hydrocarbon material end up becoming higher. In particular, when using a raw material comprised of $C_5$ raffinate which contains a dicyclopentadiene in an amount of 10 wt % or more, such a tendency becomes stronger when the pressure of the desulfurization reaction is made too high.

Further, the gas hourly space velocity (GHSV) of the cracked gasified $C_5$ raffinate of the desulfurization reaction is not particularly limited, but is preferably 50 to 500/hour, more preferably 100 to 300/hour.

Further, due to such a desulfurization step, it is possible to obtain a gasified $C_5$ raffinate from which at least part of the sulfur-containing ingredients which were contained in the cracked gasified $C_5$ raffinate is removed (below, sometimes referred to as the "desulfurized gasified $C_5$ raffinate").

Due to such a desulfurization step, it is possible to reduce the content ratio of sulfur atoms in the desulfurized gasified $C_5$ raffinate to preferably 5 weight ppm or less with respect to the desulfurized gasified $C_5$ raffinate as a whole, more preferably 3 weight ppm or less, furthermore preferably 1 weight ppm or less.

<Hydrogen Addition Step>

Next, the hydrogen addition step will be explained. The hydrogen addition step is a step of hydrogenating at least part of the carbon-carbon double bonds of at least one selected from the diolefins and olefins which are contained in gasified $C_5$ raffinate after the above-mentioned desulfurization step in the gas phase state.

In the hydrogen addition step, the hydrogenation reaction is preferably performed in the presence of a catalyst. Usually, this is performed by feeding the desulfurized gasified $C_5$ raffinate which is obtained in the above-mentioned desulfurization step into the hydrogenation reactor in which the catalyst is packed. The catalyst is not particularly limited, but in the present invention, a catalyst which has a supported nickel as its main ingredient is preferably used.

The catalyst which has a supported nickel as its main ingredient is a catalyst which comprises compound having a support comprised of a supporting inorganic compound on which a metal comprised of nickel is supported as its main ingredient. As specific examples of the support comprised of a supporting inorganic compound, silica, alumina, boria, silica-alumina, diatomaceous earth, white clay, clay, magnesia, magnesia-silica, titania, zirconia, etc. may be mentioned. Among these as well, magnesia-silica is preferable from the viewpoint of the higher hydrogenation performance. That is, in the hydrogen addition step, a catalyst which comprises, as a main ingredient, a compound where nickel is supported on magnesia-silica is preferable. By using such a catalyst, it is possible to efficiently remove the diolefins and olefins which are contained in the desulfurized gasified $C_5$ raffinate.

Further, as the metal which is supported on the support, it is possible to include, in addition to nickel, a metal other than nickel in an amount of preferably 25 wt % or less with respect to the metal which is supported on the support as a whole, more preferably 10 wt % or less, but when not including a metal other than nickel and using nickel alone, the hydrogenation performance is high, so this is more preferable.

The content ratio of the metal which is supported on the support to the catalyst as a whole is preferably 20 to 90 wt %, more preferably 40 to 70 wt %. On the other hand, the content ratio of the support comprised of the supporting inorganic compound to the catalyst as a whole is preferably 80 to 10 wt %, more preferably 60 to 30 wt %. If the content of the metal which is supported on the support is too small, the effect of improvement of the hydrogenation performance sometimes becomes hard to obtain. On the other hand, if too large, sometimes the catalyst itself falls in mechanical strength and a sufficient hydrogenation performance cannot be exhibited.

Further, the shape of the catalyst is not particularly limited and in general is a pellet shape, spherical shape, columnar shape, ring shape, etc. Further, the particle size of the catalyst is not particularly limited. The optimum value should be selected by the inside diameter of the hydrogenation reactor etc., but the average particle size of the catalyst used in the present invention is preferably 1 to 40 mm, more preferably 2 to 20 mm, from the viewpoint of the efficient progress in the hydrogenation reaction.

The hydrogenation reactor which is used in the hydrogen addition step is not particularly limited, but a multitube type fixed bed circulation reactor is preferable. Further, the inside diameter of the reaction tubes of the multitube type fixed bed circulation reactor is preferably 6 to 100 mm, more preferably 10 to 70 mm, while the length of the reaction tubes is preferably 0.1 to 10 m, more preferably 0.3 to 7 m.

In the hydrogen addition step, as pretreatment of the hydrogenation reaction, it is preferable to treat the catalyst packed in the hydrogenation reactor by reduction in the hydrogenation reactor in advance by a known method etc. The reduction method and reduction condition at the time of reduction of the catalyst in advance can, for example, be made ones similar to those in the above-mentioned desulfurization step.

In the hydrogen addition step, it is preferable to perform the hydrogenation reaction in a reducing atmosphere, in particular, it is preferable to perform it in a hydrogen gas atmosphere. By performing the hydrogenation reaction in a hydrogen gas atmosphere, it is possible to raise the efficiency of the hydrogenation reaction more. The gas hourly space velocity (GHSV) of hydrogen at the time of performing the hydrogenation reaction in a hydrogen gas atmosphere is not particularly limited, but 100 to 10000/hour is preferable, while 200 to 5000/hour is more preferable.

The temperature of the hydrogenation reaction is not particularly limited, but, from the viewpoint of efficient progress of the hydrogenation reaction, is preferably 140 to 400° C., more preferably 150 to 300° C., furthermore preferably 160 to 250° C.

Further, the pressure of the hydrogenation reaction is, by gauge pressure, preferably 0.3 MPa or less, more preferably 0.1 MPa or less, furthermore preferably 0.05 MPa or less, while is preferably 0 MPa or more. If the pressure of the hydrogenation reaction is too high, there is the inconvenience that the ingredients which are contained in the desulfurized gasified $C_5$ raffinate and which are thermally cracked in the gas-phase thermal cracking step (for example, cyclopentadiene) end up undergoing a dimerization reaction and returning to the $C_{10}$ diolefins (for example, dicyclopentadiene) before thermal cracking. Further, if ending up returned to $C_{10}$ diolefins before thermal cracking, the hydrogenation at the hydrogen addition step ends up becoming difficult and as a result the content ratios of the diolefins and olefins in the obtained hydrocarbon material ends up becoming higher. In particular, when using the raw material comprised of $C_5$ raffinate which contains dicyclopentadiene in an amount of 10 wt % or more, such a tendency becomes stronger if making the pressure of the hydrogenation reaction too high.

Further, the gas hourly space velocity (GHSV) of the desulfurized gasified $C_5$ raffinate of the hydrogenation reaction is not particularly limited, but is preferably 50 to 500/hour, more preferably 100 to 300/hour.

Further, due to such a hydrogen addition step, it is possible to obtain gasified $C_5$ raffinate from which at least part of the carbon-carbon double bonds of at least one selected from the diolefins and olefins which are contained in the desulfurized gasified $C_5$ raffinate can be removed. Further, by condensing this by a heat exchange type of cooler etc., it is possible to obtain a hydrocarbon material (gas-phase thermally cracked, desulfurized, and hydrogenated $C_5$ raffinate).

According to the present invention, it is possible to obtain a hydrocarbon material in this way.

According to the present invention, the $C_5$ raffinate is gasified to thermally crack at least part of the $C_{10}$ diolefins which are contained in the gasified $C_5$ raffinate, then is desulfurized and hydrogenated in the gas phase state, so it is possible to efficiently remove the diolefins and olefins and sulfur-containing ingredients in the $C_5$ raffinate. Specifically, the total concentration of the diolefins and olefins of the obtained hydrocarbon material can be made 0.5 wt % or less, preferably 0.3 wt % or less, more preferably 0.1 wt % or less, while, further, the content ratio of sulfur atoms can be made preferably 1 weight ppm or less, more preferably 0.5 weight ppm or less, furthermore preferably 0.1 weight ppm or less. For this reason, the hydrocarbon material which is obtained by the producing method of the present invention can be suitably used as a raw material of an ethylene cracker or a gasoline base material. That is, it is possible to return this to an ethylene center for utilization as a gasoline base material or raw material of an ethylene cracker. In such a case as well, it is possible to obtain the advantage of preventing deterioration of the catalyst in the diene removing tower installed in the refining section of an ethylene plant.

In addition, in the present invention, by treating the gasified $C_5$ raffinate which has been thermally cracked in the gas phase by desulfurization in the desulfurization step followed by hydrogenation in the hydrogen addition step, it is possible to make the lifetimes of the catalysts extremely long when using the desulfurization catalyst and hydrogenation catalyst in the desulfurization step and hydrogen addition step. Further, due to this, according to the present invention, it is possible to slash the time and costs required for regeneration or replacement of catalysts and possible to improve the productivity.

Further, in the present invention, since the desulfurization step and the hydrogen addition step are separate, it is possible to use catalysts which enable the desulfurization and hydrogenation to be performed more efficiently in the desulfurization step and hydrogen addition step respectively. Due to this, it is possible to obtain a high quality hydrocarbon material more efficiently. Further, in the present invention, since the desulfurization step and the hydrogen addition step are separate, it is possible to make the desulfurization by the desulfurization step substantially completely end, then perform the hydrogenation reaction, so it is possible to effectively prevent the hydrogenation catalyst which is used in the hydrogen addition step from ending up being poisoned by the sulfur-containing ingredients. As a result, it is possible to remarkably extend the lifetime of the hydrogenation catalyst. Further, in the present invention, since the desulfurization step and the hydrogen addition step are separate, for example, if the efficiency of the desulfurization catalyst which is used in the desulfurization step falls, it is sufficient to replace only the desulfurization catalyst. For this reason, it is possible to slash the time and costs required for regeneration or replacement of the catalysts and possible to improve the productivity.

Note that, in the present invention, all of the gas-phase thermal cracking step, desulfurization step, and hydrogen addition step are performed in the gas phase state, so the preheater, gasifier, and thermal cracker which are used in the gas-phase thermal cracking step, the desulfurization reactor which is used in the desulfurization step, and the hydrogenation reactor which is used in the hydrogen addition step do not necessarily have to be separate. A common reactor may of course be used.

Note that, in the present invention, it is preferable to perform a desulfurization step after the gas-phase thermal cracking step and further to perform a hydrogen addition step after the desulfurization step, but provision of any steps between the steps of the gas-phase thermal cracking step, desulfurization step, and hydrogen addition step is within the scope of the present art. Further, provision of pluralities of steps of the gas-phase thermal cracking step, desulfurization step, and hydrogen addition step and provision of additional steps between the steps are also within the scope of the present art.

EXAMPLES

Below, the present invention will be explained based on more detailed examples, but the present invention is not limited to these examples. Note that, below, "%" is based on weight unless otherwise indicated. Further, the tests and evaluations were performed as described below.

Example 1

(Gas-Phase Thermal Cracking Step)

Using as the $C_5$ raffinate the Raw Material 1 which is shown in the following Table 1, this was introduced by a fluid feed pump to a stainless steel gasification tube heated to 190° C. (length: 250 mm, inside diameter: 23.2 mm) to gasify the $C_5$ raffinate. Next, the gasified $C_5$ raffinate was introduced into a stainless steel thermal cracking tube heated to 350° C. (length: 250 mm, inside diameter: 23.2 mm) to thermally crack mainly the dicyclopentadiene in the $C_5$ raffinate. The cracking rate of dicyclopentadiene at this time was 99.9% or more.

(Desulfurization Step)

Next, a jacket type stainless steel reaction tube (inside diameter: 23.2 mm) was packed with a nickel-supported catalyst (made by Nikki Chemicals, N112 catalyst. supported metal: nickel 50%, copper 2%, chromium 2%, support: diatomaceous earth) 48.8 ml and a feed rate of 200 ml/min of hydrogen was introduced, whereby the catalyst was reduced in advance in a reactor heated to 200° C., then a feed rate of GHSV=207 of the cracked gasified $C_5$ raffinate obtained in the gas-phase thermal cracking step and a feed rate of 300 ml/min of hydrogen were introduced and a desulfurization reaction was performed in the gas phase. The inside temperature of the reactor at this time was 200 to 250° C., while the reaction pressure was 0.01 MPa or less.

(Hydrogen Addition Step)

Next, the obtained desulfurized gasified $C_5$ raffinate was introduced into a jacket type stainless steel reaction tube (inside diameter: 23.2 mm) in which a nickel-supported catalyst (made by Nikki Chemicals, N102F catalyst, supported metal: nickel 60%, support: magnesia-silica) 48.8 ml was packed and then treated for reduction in advance in the reactor heated to 200° C., and a hydrogenation reaction was performed in the gas phase. The inside temperature of the reactor at this time was 200 to 250° C., while the reaction pressure was 0.01 MPa or less. Further, the reaction tube outlet gas was condensed in a heat exchange type cooler to obtain a condensate.

Note that, in the present example, a circulation type reaction apparatus connecting the preheater, gasifier, and thermal cracker which were used in the gas-phase thermal cracking step, the desulfurization reactor which was used in the desulfurization step, and the hydrogenation reactor which was used in the hydrogen addition step was used.

Further, in present example, the $C_5$ raffinate was continuously fed to the above-mentioned gas-phase thermal cracking step, desulfurization step, and hydrogen addition step for continuous operation, the obtained condensate was extracted every certain time, and the extracted condensate was analyzed for composition by gas chromatography and analyzed for sulfur atom concentration by gas chromatography with a chemical luminescence type sulfur detector.

The reaction time at which the hydrogenation rate of a typical olefin produced, that is, cyclopentene, fell below 99% as a result of analysis (hydrogenation catalyst lifetime) is shown in Table 2, the results of composition analysis when the hydrogenation rate of cyclopentene fell below 99% are shown in Table 3, and the sulfur atom concentration when the hydrogenation rate of cyclopentene fell below 99% are shown in Table 4. Note that, in Table 2, the flow rate of the gasified $C_5$ raffinate and the amount of treatment per unit hydrogenation catalyst (=flow rate×lifetime) in the desulfurization step and hydrogen addition step are shown together. Further, in Example 1, even if continuously operating the system for 1500 hours, the hydrogenation rate of cyclopentene did not fall below 99%, so the results of analysis of the composition and sulfur atom concentration after 1500 hours are shown in Table 3 and Table 4.

Note that, in the present example, the composition was analyzed using a measuring device comprised of a gas chromatography apparatus with an FID detector (made by Agilent Technologies), using a capillary column comprised of HP-1 (60 m×250 μm×1.0 μm), making the sample injection: 1.0 μL, split ratio: 1/50, inlet temperature: 140° C., detector temperature: 300° C., carrier gas: helium, and carrier gas flow rate: 1.0 ml/min, starting the heating under the conditions of an oven temperature: 40° C., holding at 40° C. for 10 minutes, then raising the temperature to 250° C. at 10° C./min in rate, and, further, raising the temperature to 280° C. at 20° C./min in rate. Further, from the obtained results of analysis, the ratio of composition was found by the area ratio.

Further, the cracking rate of dicyclopentadiene was found by finding the ratios of composition of the dicyclopentadiene of the raw material and the dicyclopentadiene remaining after gas phase thermal cracking, subtracting the ratio of composition of dicyclopentadiene remaining after gas phase thermal cracking from the ratio of composition of dicyclopentadiene of the raw material, and dividing the result by the ratio of composition of the dicyclopentadiene of the raw material.

Further, in the present example, the sulfur atom concentration was analyzed using a measuring device comprised of a gas chromatography apparatus with a chemical luminescence type sulfur detector (made by Agilent Technologies), using a capillary column comprised of HP-1 (30 m×320 μm×1.0 μm), making the sample injection: 0.2 μL, split ratio: 1/50, inlet temperature: 140° C., detector temperature: 800° C., carrier gas: helium, and carrier gas flow rate: 1.0 ml/min, starting the heating under the conditions of an oven temperature: 40° C., holding at 40° C. for 10 minutes, then raising the temperature to 240° C. at 10° C./min in rate, and, further, raising the temperature to 280° C. at 20° C./min in rate. Further, from the obtained results of analysis, the sulfur atom concentration was calculated by the absolute calibration curve method.

Further, the hydrogenation rate of the cyclopentene was calculated from the ratios of the cyclopentene and cyclopentane.

Comparative Example 1

(Gas-Phase Thermal Cracking Step)

Using as the $C_5$ raffinate the Raw Material 1 which is shown in the following Table 1, the same procedure was followed as in Example 1 to perform the gas phase thermal cracking step. The cracking rate of dicyclopentadiene at this time was 99.9% or more.

(Hydrogen Addition Step)

Next, a jacket type stainless steel reaction tube (inside diameter: 23.2 mm) was packed with a nickel-supported catalyst (made by Nikki Chemicals, N112 catalyst) 33.9 ml and a feed rate of 200 ml/min of hydrogen was introduced, whereby the catalyst was reduced in advance in the reactor heated to 200° C., then a feed rate of GHSV=309 of the cracked gasified $C_5$ raffinate obtained in the gas-phase thermal cracking step and a feed rate of 375 ml/min of hydrogen were introduced and a hydrogenation reaction was performed in the gas phase. The inside temperature of the reactor at this time was 250 to 300° C., while the reaction pressure was 0.01 MPa or less. Further, the reaction tube outlet gas was condensed by a heat exchange type cooler to obtain a condensate.

Further, in Comparative Example 1, as well, in the same way as Example 1, the operation was performed continuously, the obtained condensate was extracted every predetermined time, and the extracted condensate was analyzed in the same way. Note that, in Comparative Example 1, after 355 hours from the start of continuous operation, the hydrogenation rate of cyclopentene fell below 99%, so at that point of time, it was judged that the lifetime of the hydrogenation catalyst reached its end and the continuous operation was stopped.

Comparative Example 2

(Gas-Phase Thermal Cracking Step)

Using as the $C_5$ raffinate the Raw Material 1 which is shown in the following Table 1, the same procedure was followed as in Example 1 to perform the gas phase thermal cracking step. The cracking rate of dicyclopentadiene at this time was 99.9% or more.

(Hydrogen Addition Step)

Next, a jacket type stainless steel reaction tube (inside diameter: 23.2 mm) was packed with a nickel-supported catalyst (made by Nikki Chemicals, N102F catalyst) 31.8 ml and a feed rate of 200 ml/min of hydrogen was introduced, whereby the catalyst was reduced in advance in the reactor heated to 200° C., then a feed rate of GHSV=337 of the cracked gasified $C_5$ raffinate obtained in the gas-phase thermal cracking step and a feed rate of 375 ml/min of hydrogen were introduced and a hydrogenation reaction was performed in the gas phase. The inside temperature of the reactor at this time was 250 to 300° C., while the reaction pressure was 0.01 MPa or less. Further, the reaction tube outlet gas was condensed by a heat exchange type cooler to obtain a condensate.

Further, in Comparative Example 2, as well, in the same way as Example 1, the operation was performed continuously, the obtained condensate was extracted every predetermined time, and the extracted condensate was analyzed in the same way. Note that, in Comparative Example 2, after 320 hours from the start of continuous operation, the hydrogenation rate of cyclopentene fell below 99%, so at that point of time, it was judged that the lifetime of the hydrogenation catalyst reached its end and the continuous operation was stopped.

Comparative Example 3

(Gas-Phase Thermal Cracking Step)

Using as the $C_5$ raffinate the Raw Material 2 which is shown in the following Table 1, the same procedure was followed as in Example 1 to perform the gas phase thermal cracking step. The cracking rate of dicyclopentadiene at this time was 99.9% or more.

(Hydrogen Addition Step)

Next, a jacket type stainless steel reaction tube (inside diameter: 23.2 mm) was packed with a palladium-supported catalyst (made by Nikki Chemicals, N1182AZ catalyst) 92.6 ml, the reaction tube was heated to 180° C., then a feed rate of GHSV=172 of cracked gasified $C_5$ raffinate which was obtained at the gas-phase thermal cracking step and a feed rate of 500 ml/min of hydrogen were introduced and a hydrogenation reaction performed in the gas phase. The inside temperature of the reactor at this time was 250 to 300° C., while the reaction pressure was 0.01 MPa or less. Further, the reaction tube outlet gas was condensed by a heat exchange type cooler to obtain a condensate.

Further, in Comparative Example 3, as well, in the same way as Example 1, the operation was performed continuously, the obtained condensate was extracted every predetermined time, and the extracted condensate was analyzed in the same way. Note that, in Comparative Example 3, after 4 hours from the start of continuous operation, the hydrogenation rate of cyclopentene fell below 99%, so at that point of time, it was judged that the lifetime of the hydrogenation catalyst reached its end and the continuous operation was stopped.

Comparative Example 4

(Gas-Phase Thermal Cracking Step)

Using as the $C_5$ raffinate the Raw Material 3 which is shown in the following Table 1, the same procedure was followed as in Example 1 to perform the gas phase thermal cracking step. The cracking rate of dicyclopentadiene at this time was 99.9% or more.

(Two-Stage Hydrogen Addition Step)

Next, a jacket type stainless steel reaction tube (inside diameter: 23.2 mm) was packed with a palladium-supported catalyst (made by Nikki Chemicals, N1182AZ catalyst) 83.4 ml, the reaction tube was heated to 180° C., then a feed rate of GHSV=165 of the cracked gasified $C_5$ raffinate which was obtained at the gas-phase thermal cracking step and a feed rate of 500 ml/min of hydrogen were introduced together to perform a hydrogenation reaction in the gas phase state. The inside temperature of the reactor at this time was 180 to 250° C., while the reaction pressure was 0.01 MPa or less.

Next, the obtained reaction gas was introduced into a jacket type stainless steel reaction tube (inside diameter: 23.2 mm) in which a nickel-supported catalyst (made by Nikki Chemicals, N102F catalyst) 63.7 ml was packed and then reduced in advance in the reactor heated to 200° C. by introducing a feed rate of 200 ml/min of hydrogen, and a hydrogenation reaction further performed in the gas phase. The inside temperature of the reactor at this time was 200 to 250° C., while the reaction pressure was 0.01 MPa or less. Further, the reaction tube outlet gas was condensed by a heat exchange type cooler to obtain a condensate.

Further, in Comparative Example 4, as well, in the same way as Example 1, the operation was performed continuously, the obtained condensate was extracted every predetermined time, and the extracted condensate was analyzed in the same way. Note that, in Comparative Example 4, after 1018 hours from the start of continuous operation, the hydrogenation rate of cyclopentene fell below 99%, so at that point of time, it was judged that the lifetime of the hydrogenation catalyst reached its end and the continuous operation was stopped.

TABLE 1

| Compound | | Content ratio | Raw Material 1 | Raw Material 2 | Raw Material 3 |
|---|---|---|---|---|---|
| Pentane | | (%) | 12.0 | 0.0 | 0.4 |
| Isopentane | | (%) | 10.9 | 0.9 | 0.8 |
| Cyclopentane | | (%) | 1.9 | 3.3 | 1.4 |
| 2-methylpentane | | (%) | 2.7 | 5.3 | 1.6 |
| 3-methylpentane | | (%) | 0.7 | 1.6 | 0.3 |
| n-hexane | | (%) | 1.1 | 1.8 | 0.3 |
| Cyclohexane | | (%) | 1.4 | 3.9 | 6.1 |
| Methylcyclohexane | | (%) | 0.3 | 0.7 | 8.5 |
| Olefins | 1-pentene | (%) | 2.3 | 0.9 | 0.3 |
| | Cyclopentene | (%) | 3.0 | 4.2 | 1.0 |
| Diolefins | Isoprene | (%) | 11.5 | 2.9 | 2.7 |
| | Trans 1,3-pentadiene | (%) | 5.1 | 4.3 | 0.5 |
| | Cyclopentadiene | (%) | 3.4 | 4.7 | 1.8 |
| | Dicyclopentadiene | (%) | 34.7 | 46.8 | 50.4 |
| Benzene | | (%) | 0.6 | 0.7 | 1.0 |
| $C_7$ to $C_9$ | | (%) | 0.4 | 1.5 | 4.0 |
| $C_{10+}$ | | (%) | 8.0 | 16.5 | 18.9 |

Note that, from Table 1 and Table 4, the Raw Material 1 to Raw Material 3 all had content ratios of diolefins and olefins of the same extent, had contents of sulfur atoms of the same extent as well, and could be judged as Raw materials of the same extent when judging whether the diolefins and olefins and sulfur-containing ingredients could be efficiently removed.

TABLE 2

| | Example 1 | Comp. Ex. 1 | Comp. Ex. 2 | Comp. Ex. 3 | Comp. Ex. 4 |
|---|---|---|---|---|---|
| Hydrogenation catalyst lifetime (hr) | >1,500 | 355 | 320 | 4 | 1,018 |
| Flow rate (hr$^{-1}$) | 207 | 309 | 337 | 172 | 165 |
| Amount of treatment per unit catalyst | >310,500 | 109,695 | 107,840 | 688 | 167,970 |

TABLE 3

| Compound | | Content ratio | Example 1 | Comp. Ex. 1 | Comp. Ex. 2 | Comp. Ex. 3 | Comp. Ex. 4 |
|---|---|---|---|---|---|---|---|
| Pentane | | (%) | 23.1 | 24.2 | 22.4 | 1.2 | 2.2 |
| Isopentane | | (%) | 24.4 | 24.1 | 20.7 | 0.5 | 4.4 |
| Cyclopentane | | (%) | 40.9 | 40.9 | 43.0 | 6.6 | 58.9 |
| 2-methylpentane | | (%) | 3.1 | 3.4 | 3.6 | 5.1 | 1.9 |
| 3-methylpentane | | (%) | 0.8 | 1.4 | 0.9 | 1.0 | 0.4 |
| n-hexane | | (%) | 1.3 | 0.4 | 1.5 | 1.1 | 0.4 |
| Cyclohexane | | (%) | 1.4 | 1.4 | 1.5 | 9.4 | 6.8 |
| Methylcyclohexane | | (%) | 0.2 | 0.3 | 0.3 | 1.5 | 9.0 |
| Olefins | 1-pentene | (%) | 0.0 | 0.0 | 0.0 | 0.0 | 0.0 |
| | Cyclopentene | (%) | 0.0 | 0.7 | 0.8 | 55.5 | 0.7 |
| Diolefins | Isoprene | (%) | 0.0 | 0.0 | 0.0 | 0.0 | 0.0 |
| | Trans 1,3-pentadiene | (%) | 0.0 | 0.0 | 0.0 | 0.1 | 0.0 |
| | Cyclopentadiene | (%) | 0.0 | 0.1 | 0.0 | 2.9 | 0.0 |
| | Dicyclopentadiene | (%) | 0.0 | 0.0 | 0.0 | 0.0 | 0.0 |
| Benzene | | (%) | 0.3 | 0.4 | 0.5 | 1.0 | 1.0 |
| $C_7$ to $C_9$ | | (%) | 0.3 | 0.4 | 0.5 | 5.1 | 4.0 |
| $C_{10+}$ | | (%) | 4.2 | 2.3 | 4.3 | 9.0 | 10.3 |

TABLE 4

| | Raw Material 1 | Raw Material 2 | Raw Material 3 | Example 1 | Comp. Ex. 1 | Comp. Ex. 2 | Comp. Ex. 3 | Comp. Ex. 4 |
|---|---|---|---|---|---|---|---|---|
| Sulfur atom content (weight ppm) | 43 | 45 | 44 | <0.1 | <0.1 | <0.1 | 45 | 0.2 |

From Table 1 to Table 4, the result was that in Example 1 where the $C_5$ raffinate was gasified and at least part of the $C_{10}$ diolefins which are contained in the gasified $C_5$ raffinate was thermally cracked, then was desulfurized in the gas phase state and further after that was hydrogenated, even after the elapse of 1500 hours, almost no diolefins and olefins remained and further almost no sulfur-containing ingredients were detected. That is, from the results, according to the present invention, it could be confirmed that it was possible to effectively remove the diolefins and olefins and sulfur-containing ingredients over a long period of time. In addition, from Table 2, it could be confirmed that in Example 1, compared with Comparative Examples 1 to 4, the amount of treatment per unit catalyst was also greater and the diolefins and olefins and sulfur-containing ingredients could be effectively removed.

On the other hand, in Comparative Examples 1 to 3 where no desulfurization step was performed, the performance of the hydrogenation catalyst fell in a short time, diolefins such as cyclopentadiene and olefins such as cyclopentene remained, and the catalyst had to be replaced in a short time. Further, in Comparative Example 3, the desulfurization effect was also insufficient. For this reason, in Comparative Examples 1 to 3, it was not possible to stably remove diolefins and olefins and sulfur-containing ingredients over a long time period and the productivity was low. Further, in Comparative Example 4, even when using a palladium catalyst to perform the first stage hydrogenation reaction then using a nickel catalyst to perform the second stage hydrogenation reaction, olefins such as cyclopentene remained after the elapse of a certain time so the catalyst life was not sufficient. Further, the desulfurization effect was also not sufficient. For this reason, in Comparative Example 4, it was not possible to stably remove diolefins and olefins and sulfur-containing ingredients over a long time period and the productivity was inferior.

The invention claimed is:

1. A method for producing a hydrocarbon material from a $C_5$ raffinate which is obtained as an extracted residual oil after separating at least part of isoprene by extraction distillation from a $C_5$ fraction which is produced as a byproduct when thermally cracking naphtha to produce ethylene and has $C_5$ organic compounds as main ingredients comprising,
   a gas-phase thermal cracking step of gasifying said $C_5$ raffinate which contains dicyclopentadiene in 10 wt % or more to thermally crack at least part of $C_{10}$ diolefins which are contained in the gasified $C_5$ raffinate,
   a desulfurization step, after said gas-phase thermal cracking step, of removing at least part of the sulfur-containing ingredients which are contained in the gasified $C_5$ raffinate after said gas-phase thermal cracking step in the gas-phase state, and
   a hydrogen addition step, after said desulfurization step, of hydrogenating at least part of the carbon-carbon double bonds of at least one selected from diolefins and olefins which are contained in the gasified $C_5$ raffinate after said desulfurization step in the gas-phase state, so as to obtain a hydrocarbon material with a total concentration of diolefins and olefins of 0.5 wt % or less,
   wherein said desulfurization step is performed in a reducing atmosphere under conditions of a pressure of 0.3 MPa or less and a temperature of 180 to 400° C.

2. The method for producing a hydrocarbon material as set forth in claim 1 wherein said desulfurization step is performed using a catalyst having a supported nickel as a main ingredient.

3. The method for producing a hydrocarbon material as set forth in claim 1 wherein said hydrogen addition step is performed in a reducing atmosphere under conditions of a pressure of 0.3 MPa or less and a temperature of 140 to 400° C.

4. The method for producing a hydrocarbon material as set forth in claim 1 wherein said hydrogen addition step is performed using a catalyst having a supported nickel as a main ingredient.

5. A hydrocarbon material which is obtained by the method as set forth in claim 1.

6. The hydrocarbon material as set forth in claim 5 which is a raw material for an ethylene cracker.

7. The hydrocarbon material as set forth in claim 5 which is used as a gasoline base material.

\* \* \* \* \*